(12) United States Patent
Schubert et al.

(10) Patent No.: US 11,969,565 B2
(45) Date of Patent: Apr. 30, 2024

(54) PROGRAMMABLE MEDICAL WIRE SYSTEM AND METHOD

(71) Applicants: Baylor University, Waco, TX (US); Scott & White Healthcare, Temple, TX (US)

(72) Inventors: Keith E. Schubert, China Spring, TX (US); Linda Olafsen, Waco, TX (US); Jeffrey Olafsen, Waco, TX (US); Sunghwan Lee, West Lafayette, IN (US); Jason H. Huang, Temple, TX (US); Samantha Dayawansa, Temple, TX (US); Jin-Woo Choi, Baton Rouge, LA (US)

(73) Assignees: BAYLOR UNIVERSITY, Waco, TX (US); SCOTT & WHITE HEALTHCARE, Temple, TX (US)

( * ) Notice: Subject to any disclaimer, the term of this patent is extended or adjusted under 35 U.S.C. 154(b) by 925 days.

(21) Appl. No.: 16/269,689

(22) Filed: Feb. 7, 2019

(65) Prior Publication Data

US 2019/0247629 A1 Aug. 15, 2019

Related U.S. Application Data

(60) Provisional application No. 62/628,614, filed on Feb. 9, 2018.

(51) Int. Cl.
*A61M 25/09* (2006.01)
*A61B 17/00* (2006.01)
(Continued)

(52) U.S. Cl.
CPC ....... *A61M 25/09041* (2013.01); *A61B 17/00* (2013.01); *A61M 25/0158* (2013.01);
(Continued)

(58) Field of Classification Search
CPC ........ A61M 25/09041; A61M 25/0158; A61M 2025/09075; A61M 2025/0915;
(Continued)

(56) References Cited

U.S. PATENT DOCUMENTS 4,846,573 A 7/1989 Taylor et al.
5,143,085 A 9/1992 Wilson
(Continued)

FOREIGN PATENT DOCUMENTS

EP 0 600 676 A2 6/1994
EP 0600676 A2 6/1994
(Continued)

OTHER PUBLICATIONS

Tehrani, "Modeling and Control of Steerable Ablation Catheters", The University of Western Ontario—Electronic Thesis and Dissertation Repository, Graduate Program in Electrical and Computer Engineering, May 2014, 191 pages.
(Continued)

*Primary Examiner* — Devin B Henson
(74) *Attorney, Agent, or Firm* — Jackson Walker LLP (57) ABSTRACT

The disclosure provides a system and method for a programmable medical wire that can be preprogrammed, and controlled and reshaped upon command. The system can include a power supply, a controller, and a multilayered wire assembly. The wire assembly includes a core conductor, actuator conductors coupled to the core conductor, selective conductors formed adjacent the core conductor and the actuator conductors, and a protective biocompatible shield around the layers. The selective conductors can be energized to activate the actuator conductors and cause the actuator conductors to bend or twist in a preprogrammed manner. By selectively controlling the direction of movement of the actuator conductors, the wire assembly can be remotely
(Continued)

guided through body passageways to the target. Auxiliary equipment such as sensors, micro cameras, detectors, cutters, and other equipment can also be coupled to the wire assembly, and controlled and communicated with through one or more of the selective conductors.

11 Claims, 4 Drawing Sheets

(51) Int. Cl.
*A61M 25/01* (2006.01)
*H01B 7/04* (2006.01)
*A61B 90/00* (2016.01)

(52) U.S. Cl.
CPC ...... *H01B 7/04* (2013.01); *A61B 2017/00017* (2013.01); *A61B 2017/00305* (2013.01); *A61B 2017/00318* (2013.01); *A61B 2017/00411* (2013.01); *A61B 2017/00867* (2013.01); *A61B 2017/00929* (2013.01); *A61B 90/361* (2016.02); *A61M 2025/09075* (2013.01); *A61M 2025/09116* (2013.01); *A61M 2025/0915* (2013.01); *A61M 2025/09191* (2013.01); *A61M 2205/0233* (2013.01); *A61M 2205/50* (2013.01)

(58) Field of Classification Search
CPC .......... A61M 2025/09191; A61B 2017/00318; A61B 2017/00411; H01B 7/04
See application file for complete search history.

(56) References Cited

U.S. PATENT DOCUMENTS

| | | | |
|---|---|---|---|
| 5,311,449 A | 5/1994 | Adams | |
| 5,391,147 A * | 2/1995 | Imran ................. | A61B 18/1492 600/434 |
| 6,939,338 B2 * | 9/2005 | Waldhauser ......... | A61B 1/0058 604/528 |
| 7,766,896 B2 * | 8/2010 | Kornkven Volk .... | A61M 25/09 604/527 |
| 9,168,054 B2 | 10/2015 | Turner et al. | |
| 9,370,640 B2 * | 6/2016 | Zhang .................. | A61L 31/048 |
| 10,960,182 B2 * | 3/2021 | Kim .................... | A61M 25/0113 |
| 2002/0082523 A1 | 6/2002 | Kinsella et al. | |
| 2005/0021020 A1 | 1/2005 | Blaha | |
| 2015/0065953 A1 | 3/2015 | Ducharme et al. | |
| 2015/0173837 A1 | 6/2015 | Barnett | |
| 2016/0001044 A1 * | 1/2016 | Rauch .................. | H01L 41/082 606/108 |

FOREIGN PATENT DOCUMENTS

| | | |
|---|---|---|
| WO | 2009/015013 | 1/2009 |
| WO | 2010/030991 | 3/2010 |
| WO | 2018/183832 | 10/2018 |

OTHER PUBLICATIONS

Barry, et al., "A Smart Guidewire for Smooth Navigation in Interventional Radiology", Journal of Medical Devices, Mar. 2015, vol. 9, retrieved from https://www.researchgate.net/publication/267902329_A_Smart_Guidewire_for_Smooth_Navigation_in_Interventional_Radiology, 10 pages.

Ganet, et al., "Development of a smart guide wire using an electrostrictive polymer: Option for steerable orientation and force feedback", Scientific Reports, Dec. 17, 2015, Retrieved from https://www.researchgate.net/publication/287213065_Development_of_a_smart_guide_wire_using_an_electrostrictive_polymer_Option_for_steerable_orientation_and_force_feedback, 12 pages.

Miller, Donald, "Why Use Remote Guidance to Steer Catheters and Guide Wires?", Radiology—Science to Practice, vol. 232—No. 2, Aug. 2004, 2 pages.

Lee, et al., "Pneumatic-type Surgical Robot End-effector for Laparoscopic Surgical-Operation-by-Wire", BioMedical Engineering OnLine 2014, 13:130, 19 pages.

Abbott. (n.d.). Hi-Torque Command Peripheral Guide Wire, 2019. Retrieved from https://www.cardiovascular.abbott/us/en/hcp/products/peripheral-intervention/hi-torque-command-guidewires.html.

Medtronic. (n.d.). Intuition Guidewire, 2019. Retrieved Jul. 16, 2019, from https://www.medtronic.com/us-en/healthcare-professionals/products/cardiovascular/interventional-guidewires-accessories/intuition-guidewire.html.

Boston Scientific. (n.d.). Fathom™ Steerable Guidewires. Retrieved Jul. 16, 2019, from https://www.bostonscientific.com/content/gwc/en-us/products/embolization/fathom-steerable-guidewires.html, 6 pages.

Cordis. (n.d.). AQUATRACK® Hydrophilic Nitinol Guidewire. Retrieved Jul. 16, 2019, from https://www.cordis.com/en_us/endovascular/intervene/steerable-guidewires/aquatrack-hydrophilic-guidewire.html, Steerable Guidewires on pp. 36-44.

Notification of Transmittal of the International Search Report and Written Opinion of the International Searching Authority—the European Patent Office—dated May 16, 2019 for International Application No. PCT/US2019/017025, 15 pages.

Ashammagari, Aditya Reddy, "A Framework for Automating Interventional Surgeries", Aug. 15, 2013, Thesis Submitted to the Faculty of the Graduate School of New York at Buffalo, 85 pages.

Cordis Launches Aquatrack—Vascular News, Feb. 4, 2010, retrieved from https://vascularnews.com/cordis-launches-aquatrack/, Jul. 30, 2019, 3 pages.

Boston Scientific, Fathom™ Steerable Guidewires—Revolutionizing Access Brochure, May 9, 2017, 3 pages.

Cordis—"Endovascular Catalog—U.S.", 2019, 122 pages.

Tomelleri, C., International Search Report for International Patent Application No. PCT/US2019/017025, dated May 16, 2019, European Patent Office.

Tomelleri, C., Written Opinion for International Patent Application No. PCT/US2019/017025, dated May 16, 2019, European Patent Office.

* cited by examiner

PROGRAMMABLE MEDICAL WIRE SYSTEM AND METHOD

CROSS REFERENCE TO RELATED APPLICATIONS

Not applicable

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The disclosure relates generally to medical equipment and methods of use. More specifically, the disclosure relates to a medical wire assemblies used for access through body passageways.

Description of the Related Art

In medical applications, there is often the need to reach portions of the body through the body's own passageways. The body passageways such as the ear, nose, throat, ureter, and rectal passageways allow surgeons and other medical personnel to access different portions of the body that need treatment. Other body passageways include blood vessels.

For example, aneurysms occur generally at a weakened portion of a blood vessel that further stretches the blood vessel walls. One treatment to strengthen the blood vessel walls is to insert a very fine wire into a blood vessel and follow the passageways through the body to the aneurysm. The wire can be followed through an external constantly running CT scan. The medical personnel generally move the wire back and forth. Perhaps twisting the wire one way or the other by trial and error until it hopefully hits the target area. If the wire can form a protective mass or layer inside the aneurysm in time before it burst, then the patient's health and perhaps survival is significantly increased. Thus, success as well as timing in reaching the target area is critical for the patient.

There is a need to produce a medical wire system that can be directed more easily, more reliably, and more quickly through the body passageways, including blood vessels.

BRIEF SUMMARY OF THE INVENTION

The disclosure provides a system and method for a programmable medical wire that can be preprogrammed and then controlled and reshaped upon command. The ability to reshape the wire provides the ability of the wire in a body passages to more quickly, easily, more successfully reached a target area in the body. In general, the system includes a power supply, a controller, and a multilayered wire assembly. The wire assembly includes a core conductor, a plurality of actuator conductors electrically coupled to the core conductor, a plurality of selective conductors formed adjacent the core conductor and the actuator conductors that are separated by insulation and can be selectively electrically coupled to the actuator conductors and/or core conductor, and a protective biocompatible shield around the layers. One or more of the selective conductors can be energized to activate the actuator conductors and/or core conductor and cause the actuator conductors and/or core conductor to bend or twist in a preprogrammed manner. When the conductors are de-energized, the actuator conductor and/or core conductor can resume its natural shape. By selectively controlling the direction and amount of the bend or twist of one or more of the actuator conductors and/or core conductor, and the time of the bend, the wire assembly can be remotely guided through the body passageways to the target. Auxiliary equipment, such as sensors, micro cameras, detectors, cutters, and other equipment, can also be coupled to the wire assembly, and controlled and communicated with through one or more of the selective conductors.

The disclosure also provides a method of controlling a wire assembly in a body passageway by selectively energizing conductors to actuate specific actuators to bend or twist portions of the wire assembly that are preprogrammed to respond to the energized conductors as the wire assembly moves along the body passageway.

DETAILED DESCRIPTION

The Figures described above and the written description of specific structures and functions below are not presented to limit the scope of what Applicant has invented or the scope of the appended claims. Rather, the Figures and written description are provided to teach any person skilled in the art how to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related, and other constraints, which may vary by specific implementation, location, or with time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. The use of a singular term, such as, but not limited to, "a," is not intended as limiting of the number of items. Further, the various methods and embodiments of the system can be included in combination with each other to produce variations of the disclosed methods and embodiments. Discussion of singular elements can include plural elements and vice-versa. References to at least one item may include one or more items. Also, various aspects of the embodiments could be used in conjunction with each other to accomplish the understood goals of the disclosure. Unless the context requires otherwise, the term "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The terms "top", "up', "upward', "bottom", "down", "downwardly", and like directional terms are used to indicate the direction relative to the figures and their illustrated orientation and are not absolute relative to a fixed datum such as the earth in commercial use. The term "inner," "inward," "internal" or like terms refers to a direction facing toward a center portion of an assembly or component, such as longitudinal centerline of the assembly or component, and the term "outer," "outward," "external" or like terms refers to a direction facing away from the center portion of an assembly or component. The term "coupled," "coupling," "coupler," and like terms are used broadly herein and may include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and may further include without limitation integrally forming one functional member with another in a unitary fashion. The coupling may occur in any direction, including rotationally. The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions. Some elements are nominated by a device name for simplicity and would be understood to include a system of related components that are known to those with ordinary skill in the art and may not be specifically described. Some elements are described with a given element number and where helpful to describe embodiments with Various examples are provided in the description and figures that perform various functions and are non-limiting in shape, size, description, but serve as illustrative structures that can be varied as would be known to one with ordinary skill in the art given the teachings contained herein. Element numbers with suffix letters, such as "A", "B", and so forth, are to designate different elements within a group of like elements having a similar structure or function, and corresponding element numbers without the letters are to generally refer to one or more of the like elements.

The disclosure provides a system and method for a programmable medical wire that can be preprogrammed and then controlled and reshaped upon command. The ability to reshape the wire provides the ability of the wire in a body passages to more quickly, easily, more successfully reached a target area in the body. In general, the system includes a power supply, a controller, and a multilayered wire assembly. The wire assembly includes a core conductor, a plurality of actuator conductors electrically coupled to the core conductor, a plurality of selective conductors formed adjacent the core conductor and the actuator conductors that are separated by insulation and can be selectively electrically coupled to the actuator conductors and/or core conductor, and a protective biocompatible shield around the layers. One or more of the selective conductors can be energized to activate the actuator conductors and/or core conductor and cause the actuator conductors and/or core conductor to bend or twist in a preprogrammed manner. When the conductors are de-energized, the actuator conductor and/or core conductor can resume its natural shape. By selectively controlling the direction and amount of the bend or twist of one or more of the actuator conductors and/or core conductor, and the time of the bend, the wire assembly can be remotely guided through the body passageways to the target. Auxiliary equipment, such as sensors, micro cameras, detectors, cutters, and other equipment, can also be coupled to the wire assembly, and controlled and communicated with through one or more of the selective conductors.

Figure 1:
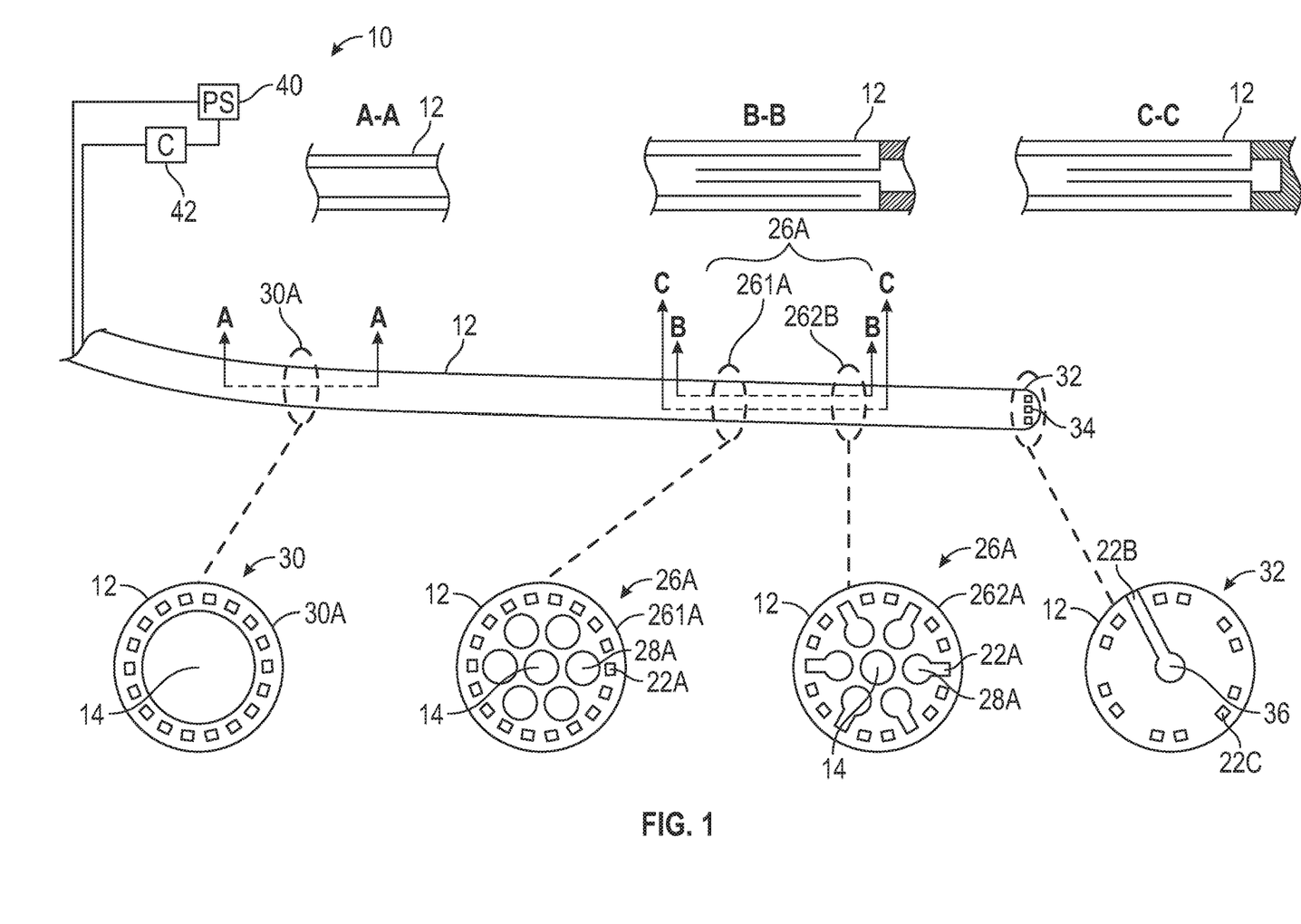
FIG. 1 is a schematic perspective view of an example of a programmable medical wire system.
Figure 2:
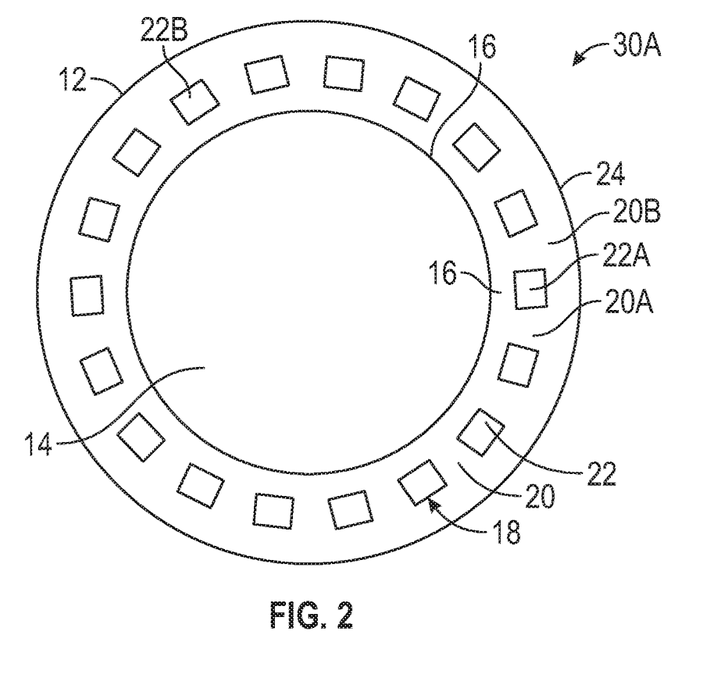
FIG. 2 is a schematic cross sectional view of an example of a selective conductor portion of the programmable medical wire system having a core conductor and selective conductors.
Figure 3A:
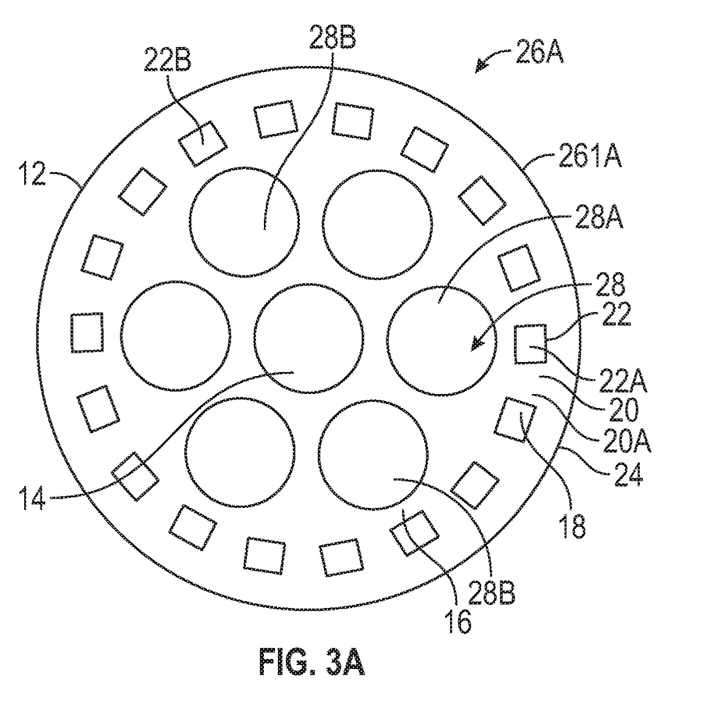
FIG. 3A is a schematic cross sectional view of an example of a transition actuator portion of the programmable medical wire system having a core conductor, actuator conductors electrically coupled to the core conductor, and selective conductors.
Figure 3B:
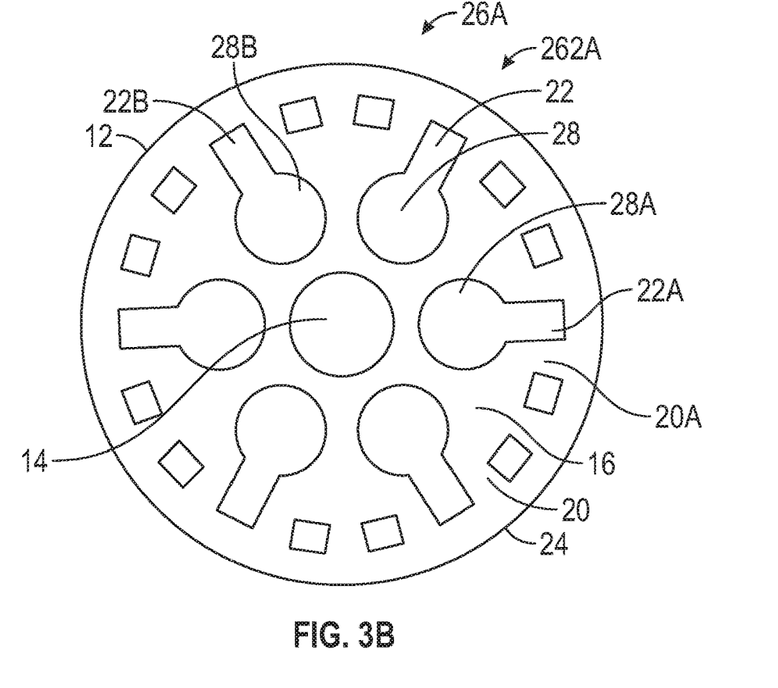
FIG. 3B is a schematic cross sectional view of an example of a coupling actuator portion of the programmable medical wire system with a core conductor, actuator conductors electrically coupled to the core conductor, and selective conductors electrically coupled to the actuator conductors.
Figure 4:
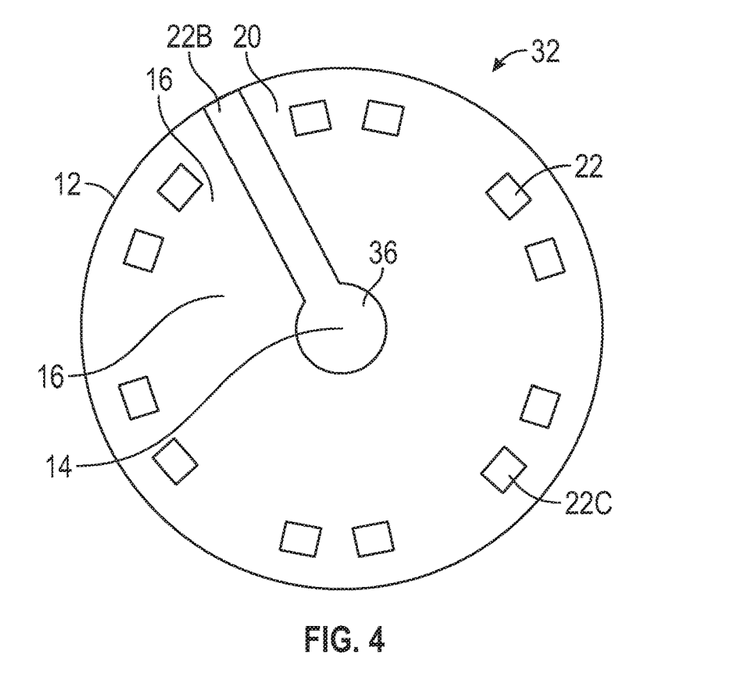
FIG. 4 is a schematic cross sectional view of an example of an equipment portion of the programmable medical wire system having a core conductor, a twist conductor electrically coupled to a core conductor, and at least one selective conductor electrically coupled to the twist conductor.

FIG. 1 is a schematic perspective view of an example of a programmable medical wire system. FIG. 2 is a schematic cross sectional view of an example of a selective conductor portion of the programmable medical wire system having a core conductor and selective conductors. FIG. 3A is a schematic cross sectional view of an example of a transition actuator portion of the programmable medical wire system having a core conductor, actuator conductors electrically coupled to the core conductor, and selective conductors. FIG. 3B is a schematic cross sectional view of an example of a coupling actuator portion of the programmable medical wire system with a core conductor, actuator conductors electrically coupled to the core conductor, and selective conductors electrically coupled to the actuator conductors. FIG. 4 is a schematic cross sectional view of an example of an equipment portion of the programmable medical wire system having a core conductor, a twist conductor electrically coupled to a core conductor, and at least one selective conductor electrically coupled to the twist conductor.

The programmable medical wire system 10 generally includes a multilayered programmable wire assembly 12 having a variety of conductors described herein, a power supply 40 for energizing conductors in the wire assembly, and a controller 42 for controlling which conductors are energized. The term "wire" is used broadly herein, and includes formed wires as well as conductors formed by deposition or other methods. The material of the "wire" can be various conductive materials, including metals, semimetals, conductive metal oxides, and other conductive materials. In general, the conductors are flexible to accommodate an amount of bending, twisting, and other movement suitable for the application. In general, the programmable wire assembly 12 is an elongated multilayer assembly having one or more portions that are preprogrammed to move laterally or rotationally (or "twist") relative to a main body of the wire assembly. In at least one embodiment, the movement can be preprogrammed by pre-setting an actuator conductor, a core conductor, or a combination thereof to move in a given manner when energized and return to a normal shape when de-energized.

In at least one embodiment, at least one selective conductor portion 30 (such as the selective conductor portion 30A shown in FIG. 1) of the wire assembly 12 is formed by a core conductor 14 with a series of layers surrounding the core conductor. The core conductor may vary in size and configuration along the wire assembly 12. The insert in FIG. 1 and the larger image in FIG. 2 show a cross section of the selective conductor portion 30A in more detail. An insulation layer 16 can be formed around the core conductor. A selective conductor layer 18 can be formed around the insulation layer 16. The selective conductor layer 18 can be radially divided into insulation portions 20 that separate selective conductors 22. For example, selective conductor 22A is bounded by an insulation portion 20A on one side and insulation portion 20B on a distal side. A further layer 24 can be formed over the selective conductor layer 18 to protect the wire assembly as a shield from external fluids and other materials. Therefore, advantageously, the layer 24 can be biocompatible and flexible to allow movement through the body passageways. One example of a suitable material is a chemical vapor deposition polymer.

In at least one embodiment, at least one actuator portion 26A (generally "26") can be formed in the programmable wire assembly 12. The actuator portion 26 can be electrically coupled with the selective conductor portion 30. In at least one embodiment, the actuator portion 26 can be formed for illustrative purposes from a transition actuator portion 261A and a coupling actuator portion 262A.

The insert in FIG. 1 and FIG. 3A shows details of the transition actuator portion 261A. The transition actuator portion 261A includes a smaller diameter core conductor 14 that is surrounded by insulation, similar to the insulation layer 16. The insulation insulates a plurality of actuator conductors 28A, 28B, and so forth (generally "28") from the core conductor 14. The actuator conductors 28 are electrically coupled to the core conductor 14 generally on a proximal end toward the selective conductor portion 30A and generally not on the distal end. Further, the actuator conductors 28 are insulated from each other to allow independent control of the actuator conductors 28 through electrical energy provided by selection of the correspondingly selective conductor(s) 22. The selective conductor layer 18 with the selective conductors 22 remains formed around the core conductor 14 as well as now the actuator conductors 28.

The actuator conductors 28 can be made of materials that change shape with temperature changes. For example and without limitation, a suitable material can be a "shaped memory effect" ("SME") material, such as nickel-titanium (nitinol). Such a material responds to heat such as through electrical stimulation through a resistive material and can return to a natural state when the heat is removed. The chemical composition can change the amount of heat that is required to produce a given movement. To program the shape, the material can be heated to a certain level, bent or twisted or otherwise formed to a desired shape, and then cooled at that shape to set the shape. The shape will resume with suitable heat. Thus, the material forms a "memory" of a heated shape.

The desired shape can thus be programmed in manufacturing of the programmable wire assembly 12. With resistive electrical energy resulting in heat in the actuator portion 26, the programmable wire assembly can move in a variety of directions depending on which actuator conductor 28 is stimulated by heat, such as through electrical current.

The coupling actuator portion 262A shown in the insert in FIG. 1 and a larger view in FIG. 3B is similarly constructed as in transition actuator portion 261A. However, the actuator conductors 28 are electrically coupled to corresponding selective conductors 22. For example, actuator conductor 28A can be electrically coupled to a selective conductor 22A. The coupling is surrounded by the insulation from insulation layer 16 and the insulation 20. Essentially, the insulation layer 16 has been bridged by coupling the actuator conductor with the selective conductor. Thus, when the actuator conductor 28A is desired to be actuated, electrical current can flow through the selective conductor 22A and heat up the actuator conductor 28A. The heat can cause the actuator conductor 28A to move in a preprogrammed manner depending on the level of heat or other energy created by the actuator conductor 28A. In a similar fashion, other selective conductors 22 can be electrically coupled with corresponding actuator conductors 28. Thus, selective actuation of one or more of the actuator conductors can cause the programmable wire assembly to move in a variety of directions. In similar manner, the core conductor can be electrically coupled with a selective conductor to flow electrical current into the core conductor to cause the core conductor to move in a preprogrammed manner if the core conductor has been preset to do so upon activation.

An equipment portion 32 of the programmable wire assembly 12 can provide further flexibility and use of the programmable wire assembly 12. In at least one embodiment, an end of the core conductor 14 can be pre-programmed into a twisted shape to form a portion as a twist conductor 36. One or more twist conductors (not shown) can be used in different locations that are coupled to the core conductor 14. The twist conductor 36 can be electrically coupled to a selective conductor 22B in similar fashion as has been described. Upon actuation of the selective conductor 22B to create heat on the twist conductor 36, the twist conductor 36 can twist along a longitudinal axis of the twist conductor (that is, along a length of the twist conductor) and rotate the programmable wire assembly depending on the amount of heat provided. In this embodiment, the twist conductor can rotate when activated the equipment portion 32. While the equipment portion 32 is used for illustration, a twist conductor 36 can be inserted at other portions along the length of the programmable wire assembly 12.

The equipment portion 32 can also be used to support equipment 34 for various functions. For example and without limitation, such equipment can include cameras, sensors, cutters, and other tools. Such equipment may be micro-sized or otherwise sized as appropriate. The equipment can be controlled and communicated with through one or more of the selective conductors.

Figure 5:
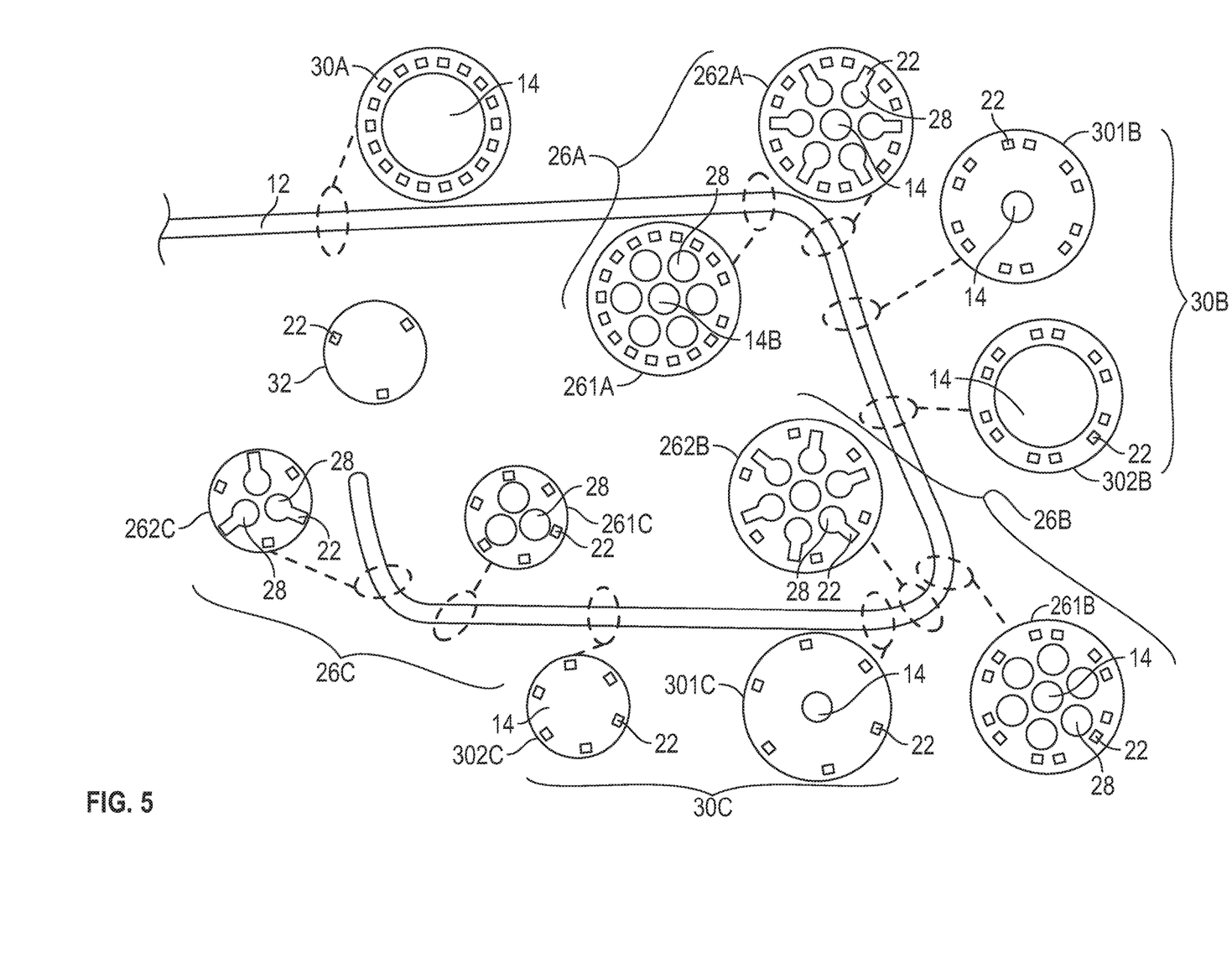
FIG. 5 is a schematic diagram of the programmable medical wire assembly with various examples of cross sections of the assembly at the noted locations.

FIG. 5 is a schematic diagram of the programmable medical wire assembly with various examples of cross sections of the assembly at the indicated locations. In some embodiments, the programmable work assembly 12 can include a plurality of selective conductor portions 30 and actuator portions 26. The actuator portions 26 can be selectively controlled by coupling different selective conductors 22 with actuator conductors 28 in each of the actuator portions 26.

In this example, the programmable work assembly 12 includes a first selective conductor portion that includes the selective conductors 22 and the core conductor 14 described above, followed by a first actuator portion 26A having the transition actuator portion 261A and coupling actuator portion 262A, as described above.

A second selective conductor portion 30B can follow the first actuator portion 26A along the programmable wire assembly 12 and is illustrated with a portion 301B and a portion 302B. A first transition conductor guide portion 301B shows the remaining selective conductors 22 that are available for subsequent control downstream without the actuator conductors 28 and selective conductors 22 that were used in the first actuator portion 26A. The first transition conductor guide portion 301B also shows the core conductor 14 that was used in the first actuator portion 26A. A second transition conductor guide portion 302B still shows the remaining selective conductors, but with a relatively enlarged core conductor 14 that can be more readily coupled to additional actuator conductors 28 in the next downstream portion.

A second actuator portion 26B can follow the second selective conductor portion 30B along the programmable wire assembly 12. The second actuator portion 26B can include a transition actuator portion 261B and coupling actuator portion 262B. The transition actuator portion 261B includes the core conductor 14 with actuator conductors 28 coupled to the core conductor and remaining selective conductors 22. The coupling actuator portion 262B is similarly constructed as the transition actuator portion 261B, but with the actuator conductors 28 also coupled to one or more of the remaining selective conductors 22. One or more of the selective conductors can be energized to actuate their corresponding actuator conductors 28 to move in one or more directions as described above.

A third selective conductor portion 30C can follow the second actuator portion 26B along the programmable wire assembly 12 and is illustrated with a portion 301C and a portion 302C. A first transition conductor guide portion 301C shows the remaining selective conductors 22 that are available for subsequent control downstream without the actuator conductors 28 and selective conductors 22 that were used in the second actuator portion 26B. The first transition conductor guide portion 301C also shows the core conductor 14 that was used in the second actuator portion 26B. A second transition conductor guide portion 302C still shows the remaining selective conductors 22, but with a relatively enlarged core conductor 14 that can be more readily coupled to additional actuator conductors 28 in the next downstream portion. The second transition conductor guide portion 302C (and others portions) also illustrates that the peripheral dimension can be reduced as appropriate as the number of selective conductors 22 and/or actuator conductors 28 is reduced in the programmable wire assembly 12.

A third actuator portion 26C can follow the third selective conductor portion 30C along the programmable wire assembly 12. The third actuator portion 26C can include a transition actuator portion 261C and coupling actuator portion 262C. The transition actuator portion 261C includes actuator conductors 28 coupled to the core conductor 14 of the third selective conductor portion 30C and remaining selective conductors 22. The coupling actuator portion 262C is similarly constructed as the transition actuator portion 261C, but with the actuator conductors 28 also coupled to one or more of the remaining selective conductors 22. One or more of the selective conductors can be energized to actuate their corresponding actuator conductors 28 to move in one or more directions as described above.

An equipment portion 32 of the programmable wire assembly 12 can provide further flexibility and use of the programmable wire assembly 12. The equipment portion 32 can also be used to support and communicate with equipment for various functions, as described above. Such equipment may be micro-sized or otherwise sized as appropriate. The equipment can be controlled and communicated with through one or more of the selective conductors 22.

The invention has been described in the context of preferred and other embodiments and not every embodiment of the invention has been described. Obvious modifications include variations in the number of components that may be combined, the number of layers and/or, conductors, shapes, and purposes, and other variations and associated methods of use and manufacture that an ordinary person skilled in the art would envision given the teachings herein. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope of the following claims.

What is claimed is:

1. A programmable medical wire system, comprising:
a programmable wire assembly, comprising:
   a core conductor;
   a first selective conductor portion comprising a first set of selective conductors and a second set of selective conductors;
   a first actuator portion comprising a first set of actuator conductors electrically coupled to the core conductor and the first set of selective conductors, the first set of actuator conductors being programmed to move toward a predetermined shape based on actuation by energy applied through selective conductors electrically coupled to the first set of actuator conductors;
   a second selective conductor portion at a different longitudinal position along the programmable wire assembly than the first actuator portion and comprising the second set of selective conductors; and
   a second actuator portion disposed at a different longitudinal position relative to the first actuator portion and configured to control movement of the programmable wire assembly independently of the first actuator portion, the second actuator portion comprising a second set of actuator conductors electrically coupled to the core conductor and the second set of selective conductors, the second set of actuator conductors being programmed to move toward a predetermined shape that is separate and independent of the predetermined shape of the first set of actuator conductors based on energy applied through the selective conductors electrically coupled to the second set of actuator conductors
wherein the energy applied through at least one of the sets of the selective conductors comprises resistive electrical energy for a heat increase that moves the actuator conductors electrically coupled to the set of selective conductors.

2. The system of claim 1, wherein the programmable wire assembly comprises a peripheral layer of a plurality of selective conductors surrounding a layer of a plurality of actuator conductors that are selectively insulated from the core conductor, wherein two or more of the actuator conductors are programmed to bend toward the predetermined shape.

3. The system of claim 1, further comprising a power supply and a controller electrically coupled to the programmable wire assembly.

4. The system of claim 1, wherein the programmable wire assembly comprises at least one equipment portion comprising one or more attachments electrically coupled to one or more selective conductors and configured to obtain medical data from use of the programmable wire assembly.

5. The system of claim 1, wherein at least one of the actuator conductors comprises a twist conductor configured to twist along a longitudinal axis of the twist conductor.

6. The system of claim 1, wherein the second actuator portion is separated from the first actuator portion by at least one cross-sectional dimension of the programmable wire assembly.

7. A method of using a programmable medical wire system, the system having a programmable wire assembly with a core conductor; a first selective conductor portion having a first set of selective conductors and a second set of selective conductors; a first actuator portion having a first set of actuator conductors being programmed to move toward a predetermined shape and electrically coupled to the core conductor and the first set of selective conductors; a second selective conductor portion at a different longitudinal position along the programmable wire assembly than the first actuator portion and having the second set of selective conductors; and a second actuator portion disposed at a different longitudinal position than the first actuator portion and having a second set of actuator conductors being programmed to move toward a predetermined shape that is separate and independent of a predetermined shape of the first set of actuator conductors and electrically coupled to the core conductor and the second set of selective conductors, the method comprising:

energizing at least one selective conductor of the first set of selective conductors to actuate at least one actuator conductor of the first set of actuator conductors in the first actuator portion to change the shape of the actuator conductor in a programmed manner from a heat increase in the actuator conductor based on an amount of thermal resistive electrical energy provided by the selective conductor;

energizing at least one selective conductor of the second set of selective conductors to actuate at least one actuator conductor of the second set of actuator conductors in the second actuator portion to change the shape of the actuator conductor in a programmed manner based on an amount of energy provided by the selective conductor in the second set of selective conductors; and controlling movement of the programmable wire assembly in the first actuator portion independently of controlling movement of the programmable wire assembly in the second actuator portion.

8. The method of claim 7, wherein the actuator conductor comprises a twist conductor and the method further comprises:

energizing a selective conductor coupled to the twist conductor; and causing the twist conductor to change shape by twisting along a length of the twist conductor.

9. A programmable medical wire system, comprising:
a programmable wire assembly, comprising:
a core conductor;
a first selective conductor portion comprising a first set of selective conductors and a second set of selective conductors;
a first actuator portion comprising a first set of actuator conductors electrically coupled to first set of selective conductors, the first set of actuator conductors being programmed to move toward a predetermined shape based on actuation by a heat increase from thermal resistive electrical energy applied through selective conductors electrically coupled to the first set of actuator conductors;
a second selective conductor portion at a different longitudinal position along the programmable wire assembly than the first actuator portion and comprising the second set of selective conductors; and
a second actuator portion disposed at a different longitudinal position than the first actuator portion and configured to control movement of the programmable wire assembly independently of the first actuator portion, the second actuator portion comprising a second set of actuator conductors electrically coupled to the second set of selective conductors, the second set of actuator conductors being programmed to move toward a predetermined shape that is separate and independent of the predetermined shape of the first set of actuator conductors by a heat increase based on thermal resistive energy applied through the selective conductors electrically coupled to the second set of actuator conductors.

10. The system of claim 9, wherein the second actuator portion is disposed at a non-adjacent longitudinal position relative to the first actuator portion.

11. The system of claim 10, wherein the second actuator portion is separated from the first actuator portion by at least one cross-sectional dimension of the programmable wire assembly.

* * * * *